(12) United States Patent
Keyser et al.

(10) Patent No.: US 8,591,469 B2
(45) Date of Patent: Nov. 26, 2013

(54) APPARATUS FOR PERIPHERAL VASCULAR ACCESS

(75) Inventors: Stephen Richard Keyser, Fresno, CA (US); James Edgerly Miller III, Fresno, CA (US); Linda Miller, legal representative, Fresno, CA (US)

(73) Assignee: I-V Access Technology, Fresno, CA (US)

( * ) Notice: Subject to any disclaimer, the term of this patent is extended or adjusted under 35 U.S.C. 154(b) by 0 days.

(21) Appl. No.: 13/331,910

(22) Filed: Dec. 20, 2011

(65) Prior Publication Data

US 2012/0150118 A1 Jun. 14, 2012

Related U.S. Application Data

(62) Division of application No. 12/319,715, filed on Jan. 9, 2009, now Pat. No. 8,105,288.

(60) Provisional application No. 61/011,211, filed on Jan. 14, 2008.

(51) Int. Cl.
*A61M 5/178* (2006.01)
(52) U.S. Cl.
USPC .................................................. 604/164.1
(58) Field of Classification Search
USPC .................................................. 604/164.1
See application file for complete search history.

(56) References Cited

U.S. PATENT DOCUMENTS

| | | | |
|---|---|---|---|
| 3,347,232 A | 10/1967 | Ginsburg | |
| 4,565,545 A | 1/1986 | Suzuki | |
| 4,588,398 A | 5/1986 | Daugherty et al. | |
| 4,629,450 A | 12/1986 | Suzuki et al. | |
| 5,242,410 A | 9/1993 | Melker | |
| 5,445,617 A * | 8/1995 | Yoon | 604/164.12 |
| 5,618,272 A | 4/1997 | Nomura | |
| 5,843,046 A | 12/1998 | Motisi et al. | |
| 6,607,511 B2 * | 8/2003 | Halseth et al. | 604/164.08 |
| 2006/0200083 A1 * | 9/2006 | Freyman et al. | 604/181 |
| 2007/0250037 A1 * | 10/2007 | Brimhall et al. | 604/512 |

FOREIGN PATENT DOCUMENTS

WO WO 03/013627 2/2003

* cited by examiner

*Primary Examiner* — Jason Flick
(74) *Attorney, Agent, or Firm* — Gary Baker; Quine Intellectual Property Law Group, P.C.

(57) ABSTRACT

This invention provides devices and methods for insertion of a catheter into a vessel. The devices include coaxial slidably mounted needle, dilator and catheter components. The methods include piercing a vessel with the needle component, dilating the pierced hole with the dilator component, retraction of the needle component, insertion of the catheter and withdrawal of the dilator.

9 Claims, 13 Drawing Sheets

APPARATUS FOR PERIPHERAL VASCULAR ACCESS

CROSS-REFERENCE TO RELATED APPLICATIONS

This application is a Divisional application claiming priority to and benefit of a prior to parent application Ser. No. 12/319,715, An Apparatus for Peripheral Vascular Access, by Stephen Richard Keyser, et al., filed Jan. 9, 2009, which claims priority to and benefit of a prior U.S. Provisional Application No. 61/011,211, An Apparatus for Peripheral Vascular Access, by Stephen Richard Keyser, et al., filed Jan. 14, 2008. The full disclosure of the prior application is incorporated herein by reference.

FIELD OF THE INVENTION

The invention is directed to methods and devices to facilitate insertion of a catheter into a vessel. Devices include axially concentric assemblies of a piercing needle and a flexible dilator that can guide an outer catheter into a vessel, such as a blood vessel. The proximal hub ends of such assemblies can have water triggered needle retraction mechanisms and/or lock mechanisms to control needle positioning during catheterization processes.

BACKGROUND OF THE INVENTION

Early technology for vascular access required surgical opening of the skin, viewing of the vessel to be catheterized, and placement, under sterile procedure of a stainless steel needle. After the insertion process, the skin was approximated and the access site covered to prevent infection. The process required a competent physician, and was indicated only in rare instances when the patient required IV sustenance or required replacement fluids in association with major surgery.

Improved technologies followed wherein the vessel was accessed by insertion of a stainless steel needle directly through the skin into the vessel. The insertion needle was left in place, covered by a protective cover, and taped in place to prevent dislodging or movement. Should significant movement of the rigid needle take place, the vessel could be punctured from the inside causing a hematoma to form in the surrounding tissue with associated pain and discomfort to the patient. While this technique was much simpler than surgical placement of the needle, it still required significant skill for correct needle insertion, and substantial restriction of patient movement to prevent complications from the stainless steel needle damaging the vessel or becoming displaced from the vessel.

More recent technologies are represented by devices with a tough, flexible plastic catheter positioned coaxially over a stainless steel guide needle. The stainless steel guide needle is inserted through the patient's skin to puncture one wall of the targeted vessel far enough for the catheter to also penetrate the vessel wall. The guide needle is then withdrawn, leaving only the plastic catheter in the vessel. The relatively flexible catheter can then be carefully slid further into the vessel without causing vessel damage or additional pain to the patient. This technology represented a significant improvement over prior techniques for long term vascular access and improved comfort to the patient. However, for catheterizations that involve relatively high rates of fluid transfer, relatively large bore catheters are required. For patients having small or "hard to find" vessels the caregiver must exercise significant skill and care to successfully introduce the relatively large bore guide needle into a vein. Failed insertions can be common is such circumstances. Partial puncture into the side of the vessel or a complete miss of the targeted vessel can require a one or more additional attempts, causing pain and suffering for the patient, and substantial anxiety for the caregiver.

To simplify procedures and reduce the stress associated with intra-vascular catheterization, many catheter devices have been conceived. For example, in U.S. Pat. No. 4,588,398, to Daugherty et al., designed a particular geometry for the leading edge of the catheter to minimize the force needed to penetrate the skin and vessel wall as the guide needle punctures each layer. Catheter materials and surface coatings were further defined to minimize catheter wall thickness and reduce friction as the catheter is inserted and the guide needle retracted. While the materials cited have provided improved comfort in intra-vascular catheters, the guide needle has continued to be a major source of pain and complications for catheterization procedures.

In other improvements, guide needle tip geometry has been developed to reduce the puncture force required to insert the guide needle through the skin and penetrate the vessel wall. Suzuki defined a tip geometry, in U.S. Pat. No. 4,565,545, that incorporates a tapered outside diameter in the needle tip as well as beveled tip angles that reduce puncture force and reduce hematosis resulting from the smaller lumen created in the blood vessel wall. In U.S. Pat. No. 5,618,272, Nomura described a guide needle in which the outer diameter of the needle is reduced immediately after the beveled distal end of the needle. The distal end of the catheter is positioned at this reduced diameter section of the needle so that the catheter insertion requires very little additional force to fully penetrate the vessel. This reportedly results in almost no additional pain once the needle has been inserted. Both of these guide needle designs rely on a relatively large bore needle diameter as required by the inner diameter of the catheter needed for the procedure. So the problems of initial pain at the time of skin and vessel puncture, as well as the difficulty of finding and successfully penetrating the targeted vessel remain as key sources of anxiety for the patient and the caregiver.

Suzuki, et al., (U.S. Pat. No. 4,629,450) improved the catheter design for certain catheterization operations by including a dilator element between a relatively small diameter guide needle and the catheter. Upon removal of the guide needle, a guide wire is inserted through the dilator into the vessel, wherein it is positioned inside the blood vessel or further advanced to within a body organ. The catheter is subsequently inserted over the dilator, through the lumen in the vessel, and over the guide wire to direct its desired position. The use of a relatively small diameter guide needle allows for less painful puncturing of the skin and vessel, while the dilator expands the puncture to facilitate introduction of a larger bore catheter. Although this design may be suited for procedures requiring insertion of a guide wire, the geometry of the dilator and its insertion technique make it difficult to position a fluid intra-vascular catheter in the vessel without blood leakage since the means of advancing the needle, advancing the dilator, retracting the needle, further advancing the dilator, advancing the catheter, and then finally retracting the dilator is time consuming, can introduce pathogens or allow blood to escape, and requires extensive technician training.

With many of the described catheterization technologies, blood contamination is risked when an intra-vascular catheter is inserted. Blood flashback can escape the catheter hub when the guide needle is removed and before the intra-vascular solution tubing can be connected, thus exposing the caregiver and patient to blood leakage. Several notable valve designs have been patented to reduce this blood leakage. For example, in U.S. Pat. No. 4,387,879, Tauschinski describes a self sealing elastomeric disc that can be incorporated into a connector body to interface with a parenteral supply solution and an intra-vascular catheter. Similarly, Motisi et al, describe a one way valve in the body of a catheter apparatus in U.S. Pat. No. 5,843,046. However, the necessity of a plunger and introduction of needle or tubing through the plunger decreases the inside diameter of the catheter and reduces the fluid flow rates for this design. An "O" ring in the valve can prevent leakage from around the plunger, but this decreases the inside diameter of the large bore catheter. The valve is held in place by a "cap" which puts its placement deeper into the throughbore, out of reach of conventional intra-vascular tubing or conventional syringes. The "cap" also prevents connection to conventional tubing or conventional syringes. This valve is bulky and decreases the size of the intra-vascular catheter. It also cannot be opened by conventional devices used by those skilled in the art.

In light of the problems remaining in the art, it would be beneficial to have relatively simple catheter insertion devices that minimize possibilities of blood contamination or escape. It would be desirable to have comfortable catheters that minimize the possibility of causing a hematoma. The present invention provides these and other features that will be apparent upon review of the following.

SUMMARY OF THE INVENTION

The present invention relates generally to the field of peripheral vascular access and more specifically to an apparatus by which a large bore intra-vascular catheter can be inserted using a smaller bore needle and dilator guide. The invention includes methods and devices that allow a guide needle to be safely retracted to avoid a second penetration of a catheterized vessel.

It is an object of this invention to provide an intra-vascular catheter apparatus that utilizes a relatively small bore guide needle and guide dilator to make insertion of an intra-vascular catheter easier to achieve and less painful for patients than conventional intra-vascular guide needles and catheters. It is another object of this invention to provide an intra-vascular catheter apparatus that employs a means of shielding the guide needle tip after insertion into the target vessel to prevent the needle tip from damaging or penetrating the opposite wall of the vessel during final catheter placement. It is another object of this invention to provide an intra-vascular catheter apparatus with a one way valve that prevents blood leakage after the catheter has been inserted into the patient's vessel, the guide needle is fully retracted, and as the intra-vascular fluid connection is attached to the catheter hub. These and other objects of this invention are achieved by an intra-vascular catheter apparatus comprising a guide needle having a distal end with a tapered and/or beveled puncturing/piercing tip and a proximal end onto which is attached a hub, and a smooth section connecting the distal and proximal ends, and a guide dilator with an inside diameter approximately the same as the outside diameter of the guide needle, a tapered distal end and a proximal end connected to a hub shaped such that a portion of the guide needle hub fits concentrically and slides axially within the dilator hub. The length of the guide dilator can be such that the guide needle, when fully inserted into the catheter, protrudes only enough to expose the beveled and/or tapered piercing tip of the needle. The apparatus further can include an intra-vascular catheter, the length of which is such that the guide dilator, when fully inserted into the intra-vascular catheter, protrudes only enough to expose the tapered tip of the guide dilator. The intra-vascular catheter can have an inside diameter the same as the outside diameter of the guide dilator, a tapered distal end, and a proximal end connected to a hub that provides a fluid-tight seal between the inside of the catheter and the exterior of the dilator hub.

The hub of the intra-vascular catheter can contain a valve or seal, made from an elastomeric plastic or rubber, generally conical in shape but with a flat round mounting flange, having one or more slits through the apex of the cone. When a hypodermic needle, catheter, or intra-vascular solution tubing is inserted into the apparatus the orifice formed in the valve can conform to the surface geometry of the device inserted through it. In preferred embodiments, the valve is positioned within the intra-vascular catheter hub so that the apex of the cone lies closer to the distal end of the catheter than the valve flange does.

Placement of the intra-vascular catheter into a patient's blood vessel can be accomplished by first inserting the tip of the guide needle through the skin and penetrating the vessel wall, followed by the tapered distal tip of the guide dilator. The guide needle can then be retracted back into the guide dilator, e.g., until the hub of the guide needle contacts a mechanical stop in the guide dilator hub. At that point, the guide needle tip is preferably covered by the guide dilator. A spring loaded stop tab in the guide needle hub can prevent the needle from becoming exposed again and possibly piercing the other wall of the vessel. The guide dilator can be inserted further into the vessel, e.g., along with the tapered distal tip of an intra-vascular catheter to penetrate the wall of the vessel to a desired position of full insertion. The guide dilator, with the guide needle safely enclosed within, can be fully withdrawn from the intra-vascular catheter hub. A resilient valve, with an orifice forming a liquid-tight seal against the exterior surface of the guide dilator hub, can have sufficient elasticity to close when the needle and dilator are fully withdrawn, thereby preventing blood leakage from the catheter proximal opening.

The present invention can include methods of inserting a catheter into a vessel using a guide needle and guide dilator. For example, a rigid hollow guide needle can be provided slidably mounted within a resilient guide dilator, which in turn is slidably mounted within a catheter intended for placement in the vessel. The piercing end of the needle can extend out from a distal end of the dilator, and the distal end of the dilator can extend out from a distal end of the catheter. The piercing end of the needle can be inserted through a wall of a vessel at an insertion point followed by insertion of the dilator distal end through the insertion point. The guide needle can be removed from the dilator or partially retracted within the dilator. The distal end of the catheter can be inserted through the insertion point into the vessel for functional placement for clinical use.

The resilient dilator can be pushed along the lumen of the vessel after the needle is removed or retracted. This dilator can safely progress along the vessel and act as a resilient guide for later further insertion of the catheter. Once the catheter is in place, the dilator can be removed (slid out) from within the catheter. Optionally, a guide wire can be introduced through the bore of the dilator, e.g., to act as a guide for the dilator. However, in preferred embodiments, a guide wire is not placed within the guide dilator. Ultimately, the catheter is inserted into the vessel, e.g., before the needle is removed from the dilator or after the needle is removed, but typically while the dilator is still inserted within the vessel.

In another embodiment of the invention, a hollow needle, dilator and catheter are in the vessel at once during the catheter insertion procedure. For example, a composition for installation of a catheter can include a hollow vessel, and an assembly comprising a rigid hollow guide needle slidably mounted within a resilient guide dilator slidably mounted within a catheter, wherein the distal end of the dilator extends out from a distal end of the catheter. Such an assembly can be inserted through an insertion point of the vessel with at least the distal end of the catheter within a lumen of the vessel. Typically, the vessel is a blood vessel. In many embodiments, the distal end of the needle extends out from the dilator; alternately, the distal end of the needle does not extend out from the dilator. In a preferred embodiment, the piercing end of the needle is inside the dilator and inside the vessel so that the piercing end can not further pierce the vessel. Alternately, the piercing end of the needle can extend out from the distal end of the dilator, or the piercing end can be inside the dilator but retracted to a position outside the vessel. In optional embodiments, the dilator and catheter each comprise a cross-sectional diameter, and the dilator and catheter each run along the vessel lumen a distance at least 5 times their respective diameters.

In other aspects of the invention, the insertion assembly (catheter insertion device) includes a transparent chamber in fluid contact with the bore of the hollow guide needle at a proximal end of the needle so that a fluid flowing from the bore can be observed. The guide dilator can further include a proximal hub traversed with a septa resiliently sealed about an outer surface of the needle. The IV-catheter can optionally further include a proximal hub traversed with a septa resiliently sealed about an outer surface of the dilator.

Other aspects of the invention provide mechanisms to retract the guide needle and/or control the movement of the needle. For example, the catheter insertion assembly can include a needle slide and lock mechanism. A catheter insertion assembly can include, e.g., a resilient guide dilator having a hub at the proximal end and a first capture element on an inner surface of the hub. The assembly can also include a rigid guide needle having a distal piercing end, an axial bore, and a second capture element, wherein the guide needle is slidably mounted within a bore of the dilator so that, in a first position, the distal piercing end of the needle extends out from a distal end of the dilator; and, in a second position, the distal piercing end of the needle is retracted within the bore of the dilator with the second capture element engaging the first contact element to hold the needle in the retracted position. In an exemplary embodiment, the first capture element is a tang under radial tension and the second capture element is a capture cavity. Alternately, the first capture element is a capture cavity and the second capture element is a tang under radial tension. In some embodiments, the dilator hub can further include a slot along which the first capture element tang slides, or along which a second guide needle tang slides, thereby allowing the needle to slide axially within the dilator, and directing the tang end to the capture slot and/or not allowing the needle to rotate about a needle bore axis within the dilator.

In other embodiments of the assembly for insertion of a catheter, retraction of the guide needle can be automatic on entry into the vessel. For example, a water triggered release detent can let the needle slide proximally on contact with vessel fluid. Of course, "water triggered" can encompass triggering by aqueous solutions and/or suspensions, not just pure water. In one embodiment, a catheter insertion assembly includes a guide dilator with a hub at the proximal end; a rigid guide needle slidably mounted within the dilator and having a distal piercing end, an axial bore, and a needle proximal end; a spring-loaded actuator urging the needle proximally relative to the dilator; and a water triggered detent positioned between the needle and dilator hub preventing the needle from sliding proximally. In a first position, the distal piercing end of the needle extends out from a distal end of the dilator. In a second position, the distal piercing end of the needle is retracted within the bore of the dilator. On contact with an aqueous fluid flowing from the needle axial bore, the detent allows the needle to slide proximally relative to the dilator in response to the urging of the actuator, thus retracting the needle when vessel fluid exits the proximal end of the needle bore. In exemplary embodiments, the actuator can be a spring, a torsion bar, shape memory alloy, a thermally actuated material, a hydrophilic polymer, a spring-loaded lever, a pressurized gas, a compressed foam, and/or the like. In exemplary embodiments, the water triggered detent can comprise a water soluble material that dissolves on contact with the fluid, a dry solid that softens when hydrated, a frictional material that becomes slippery on contact with the fluid, and/or the like. It is envisioned that the water triggered concept can apply to other embodiments wherein triggering can be by other solvents, e.g., such as non-aqueous solvents.

In another aspect of the invention, the needle can be retracted by the force of an expanding actuator material. For example, a catheter insertion assembly can include a guide dilator comprising a hub at the dilator proximal end; a rigid guide needle slidably mounted within the dilator and comprising a distal piercing end, an axial bore, and a needle proximal end; and a contracted actuator capable of expanding in response to heat or moisture to urge the needle from a first position proximally relative to the dilator to a second position. In the first position, the distal piercing end of the needle extends out from a distal end of the dilator. In a second position, the distal piercing end of the needle is retracted within the bore of the dilator. The actuator can be designed to urge the needle to slide proximally relative to the dilator on contact of the actuator with a warm or aqueous fluid, e.g., blood flowing from the needle bore. Exemplary actuator structures that can function in this embodiment include hydrogels, dry compressed foams, shape-memory alloys, dehydrated hydrophilic polymers, and/or the like.

DEFINITIONS

Unless otherwise defined herein or below in the remainder of the specification, all technical and scientific terms used herein have meanings commonly understood by those of ordinary skill in the art to which the present invention belongs.

Before describing the present invention in detail, it is to be understood that this invention is not limited to particular devices or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a component" can include a combination of two or more components; reference to "fluids" can include mixtures of fluids, and the like.

Although many methods and materials similar, modified, or equivalent to those described herein can be used in the practice of the present invention without undue experimentation, the preferred materials and methods are described herein. In describing and claiming the present invention, the following terminology will be used in accordance with the definitions set out below.

The term "vessel", as used herein, refers to a conduit through which a fluid travels. For example, a typical vessel can be a blood vein, artery, or lymph vessel. In some aspects of the invention, a vessel can be a segment of the digestive tract, a gland duct or a cerebral-spinal fluid chamber. In a more generic context, a vessel can be a chamber or conduit containing a fluid.

The "distal" end of a device component is the end closest to the patient, in use, e.g., the end of the component intended to enter a vessel first. For example, the distal end of a guide needle is the piercing end. The distal end of a dilator or catheter is the end intended to be inserted into a patient's skin or vessel.

The "proximal" end is the end of the device component oriented opposite the distal end. For example, the proximal end of a catheter insertion assembly can include the ends of the components not intended for insertion into the patent, such as the dilator hub end, or guide needle hub end.

A needle is said to be "retracted", e.g., within a dilator, when the needle is repositioned proximally relative to the dilator. Retracted needles are typically retracted proximally at least to the point where the piercing tip is within the dilator.

A "resilient" material tends to return to its original position when a deforming force is removed. A resilient seal typically comprises a seal formed when a device component is forced to slide through and deform a resilient seal component, so that the resilient component is urged against the surface of the device component leaving no space therebetween. Typical resilient seals include resilient septa, sleeves and/or o-rings. A resilient dilator or catheter is characterized by an ability to resiliently flex and bend along the central axis, e.g., to reduce physical stresses at an insertion site and/or to conform with the path of a vessel into which they are inserted.

Components of a catheterization device are "slidably mounted", e.g., when inner and outer components can be axially rotated and/or axially translated relative to each other.

An "axis", as typically used herein, is an imaginary line parallel to and in the center of a tubular device. The term axial thus refers to the direction that runs parallel to the axis, e.g., of a tubular device.

A beveled tip is the tip of a guide needle that is formed by a diagonal cut across the distal end of the needle, forming a sharpened edge that is used for piercing.

A catch is a mechanical feature on a device that stops and prevents a movement of one device relative to another. The catch can take any of a variety of forms and shapes, but is designed so that if the position of one device changes relative to another and a catch is contacted, further movement of the one device relative to the other is prevented.

Two components are concentric when their major axes are coincident.

A typical guide dilator is a long, slender, tubular device, usually made of a flexible plastic, that fits concentrically over a guide needle so that the inside diameter of the guide dilator contacts the outside diameter of the guide needle and typically can slide over the guide needle. A guide dilator is typically mounted within a catheter intended for placement in a vessel, e.g., with the dilator removed.

A hub is a part of a catheter, dilator or guide needle at the proximal end, which typically flares out to a larger internal diameter. The hub can provide a base for mounting or employing features, such as detents or needle retractor devices, catches, valves, etc. The hubs can provide functional interaction of the catheter or catheterization device with external devices, such as, e.g., trocars, syringes, fluid administration lines, optic fibers, vacutubes, etc.

An intra-vascular catheter is typically as is understood in the art. The IV catheter can include a long, slender, tubular body, usually made of a flexible plastic that fits concentrically over the guide dilator so that the inside diameter of the intra-vascular catheter contacts the outside diameter of the guide dilator. Typically, the catheter is slidably mounted allowing it to slide over the guide dilator outer surface.

A guide needle is a tubular device, e.g., usually made of stainless steel, that has a sharpened tip at its distal end that is used to puncture the skin and a targeted blood vessel, creating a hole through which a catheter may be guided. In the catheterization devices of the invention, the needle is typically a guide needle concentrically and slidably mounted within a guide dilator.

A spring tab is a mechanical feature on a device that requires a constraining force to hold it in a retracted position, but when the constraining force is removed the feature extends or moves into a desired position to act as a catch or a tab stop. The spring tab may be designed in any of several different ways known in the art, any of which provides the same function.

A tab stop is a mechanical feature on a device that prevents movement, or further movement in one direction, of one device relative to another. The tab stop may be designed in any of several different ways, any of which provides the same function.

A tapered tip in the context of the invention is a tip of a catheter, dilator or guide needle whereby the outside diameter of the tube decreases approaching the distal end, thus making the tube wall thinner. During piercing or insertion through skin or a vessel wall, a tapered tip can facilitate expansion of a pierced hole from one diameter to a larger diameter.

A valve is a device that controls the flow of fluid through the apparatus.

A flash cup is a mechanical feature that may be incorporated into the guide needle hub, allowing the caregiver to detect when the vessel wall has been punctured by virtue of vessel fluid filling the flash cup chamber.

BRIEF DESCRIPTION OF THE DRAWINGS

The drawings here shown include exemplary embodiments of the invention. It is to be understood, however, that the present invention may be embodied in various forms. Some aspects of the invention may be shown exaggerated or enlarged in the drawings to facilitate an understanding of the invention.

DETAILED DESCRIPTION

Figure 1:
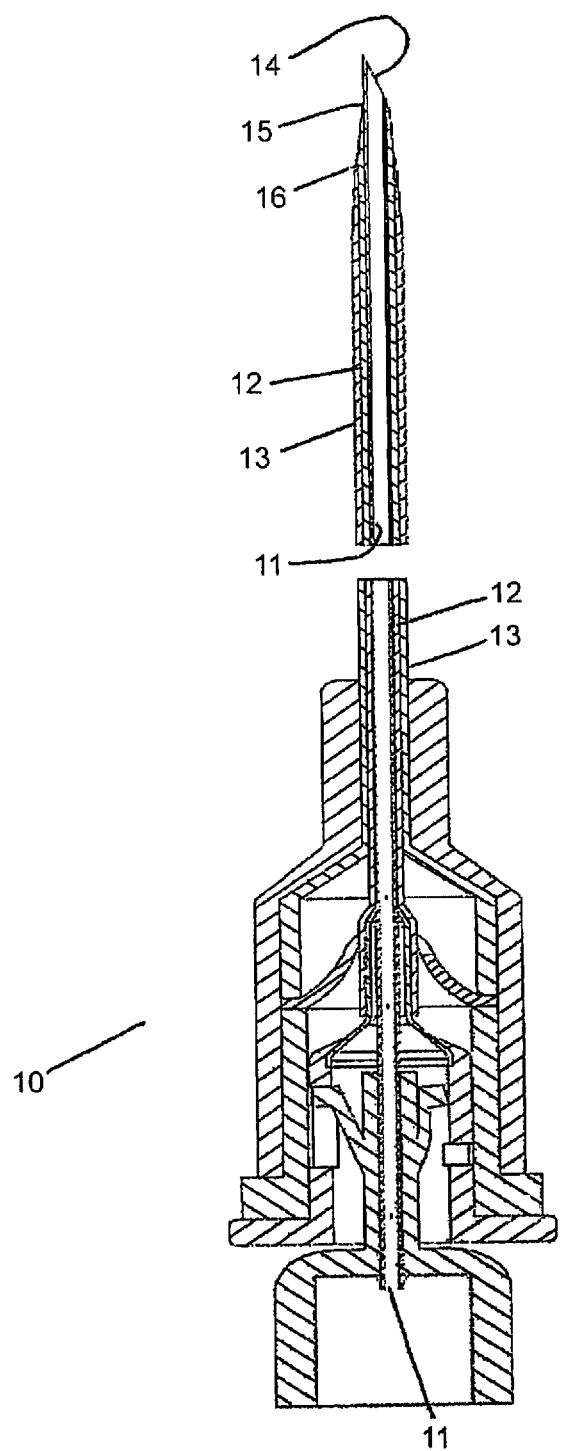
FIG. 1 is schematic diagram cross sectional view of one embodiment of the present invention including a guide needle slidably mounted within a guide dilator mounted within a catheter; each comprising a proximal hub.

The present inventions are directed to devices and methods to facilitate accurate and comfortable insertion of catheters. The catheter insertion devices can incorporate a number of features to simplify the task of catheter insertion, e.g., through conduit walls. The methods can employ devices of the invention and sequential steps to insert a catheter into a vessel.

The catheter insertion devices generally include a three-part compliment of concentric conduits to pierce and dilate an insertion point into a vessel for ultimate insertion and placement of a catheter. The invention can further include features to sanitize, simplify and inform the catheter insertion technician. The catheterization device can have a concentric needle, dilator and catheter for progressive insertion and placement of the catheter within a vessel. The components can be slidably mounted and hermetically sealed with respect to each other. The components can include proximal and distal ends specialized for insertion, retraction steps and/or functional connection with external devices, such as IV lines, drug administration ports, electrodes, surgical devices, and the like.

The methods of placing catheters can include provision of a catheter insertion device, piercing a clinical patient's skin and/or vessel, dilating the pierced point and positioning the catheter within the vessel. The catheter insertion device can include three complimentary concentric conduits with features and functions that facilitate catheter placement. For example, a rigid sharp needle can be slidably mounted within a flexible dilator layer having a tapered tip and mounted within a catheter intended for placement. The needle can pierce and initially dilate a hole in the wall of a vessel. The device can be urged forward so that the tapered end of the dilator can smoothly intrude into the hole and expand the hole circumference. Once the dilator is within the vessel, the needle can optionally be retracted or withdrawn entirely from the device. The dilator can support entry of a tapered catheter distal end into the vessel through the hole. The dilator can optionally be inserted some distance along the internal lumen of the vessel without risk of trauma to the vessel interior and provide a guide for extended insertion and placement of the catheter.

Catheter Insertion Devices

As mentioned above, the catheter insertion devices generally include at least three concentric conduits. A central guide needle is typically rigid and hollow with a sharp distal tip for initial penetration of a vessel wall. The guide needle is typically sealed and slidably mounted within the axial bore of a cylindrical flexible guide dilator. The guide dilator is typically sealed and slidably mounted within the axial bore of a catheter to be placed in a vessel (or body cavity) of a clinical patient. The distal ends of the three components are usually tapered to smoothly expand a point of entry into the vessel as the device is pushed into the vessel. The proximal ends often include a radially expanded hub useful in manipulation of the components, to provide mounting structures for device accessories and/or to provide connections to external conduits and devices.

The three major components of the device can be configured so that the tapered end of each is immediately followed by the tapered end of the next component. Alternately the needle and/or dilator components can extend some distance with a constant diameter segment exposed. For example, a guide needle configured for insertion can have only the piercing needle tip protruding from the distal end of the dilator. Optionally, the needle can extend some distance from the distal end of the dilator, exposing a constant diameter portion of the needle beyond the dilator. Similarly, the guide dilator can be configured so that only the tapered tip protrudes from the distal end of the catheter. Or, the dilator can extend some distance from the distal end of the catheter, exposing a constant diameter portion of the dilator, e.g., cylindrical body, beyond the catheter distal tip.

Vessels

The catheter insertion devices of the invention are generally intended for use in placement of a catheter in a blood vessel. However, devices of the invention, e.g., provided in the appropriate range of sizes, can facilitate insertion and/or placement of conduits through various barriers. For example, the "catheter" can be a trocar providing an access port for laparoscopic investigations or minimally invasive surgeries. The catheter can enter a vessel and progress within the vessel to a desired location some distance from the insertion point, e.g., for organ imaging, angioplasty or stent placement. In the most common embodiment, the "catheter" is essentially a semi-rigid large bore hypodermic conduit placed in a vein for fluid replacement and drug administration access. In alternate embodiments, the "vessel" is not a part of a living organism.

In most cases, the vessel penetrated by the device is a conduit through which a fluid passes. For example, the vessel for catheter placement can be a vein, an artery, a lymph vessel, a portal vessel, or a gland duct. Optionally, the vessel can be a portion of a gastro-intestinal tract, respiratory tract, or a cerebral-spinal fluid compartment. The vessel can be a body compartment, such as, e.g., an ocular chamber, peritoneum, synovium, tympanum, and the like. Optionally, the devices of the invention can be used to gain access to channels or compartments not associated with animals, such as, e.g., plant vessels and chambers, or mechanical equipment chambers or conduits.

Guide Needles

Guide needles are typically employed in the devices for catheter insertion to provide a central rigid structure with a piercing tip functioning to provide confident control in piercing of skin and a vessel wall. Further, the guide needle typically provides a support structure or path to lead a dilator and/or catheter into the vessel. Guide needles can include a hub configured, e.g., for visual confirmation of vessel entry, interaction with external devices and/or positioning control relative to other device components.

Guide needles are usually rigid hollow structures with a pointed piercing distal end. In most embodiments of the invention, the guide needle is slidably mounted within a dilator and/or catheter. Guide needles are typically cylindrical conduits with a circular cross section, or optionally can have cross sections of other shapes. The guide needles can be made from, e.g., stainless steel, a glass, ceramic, rigid plastic, and/or the like. Guide needles can range in length, e.g., from more than about 20 cm to about 0.5 cm, 10 cm to about 1 cm, from about 7 cm to about 2 cm, from about 5 cm to about 3 cm or about 4 cm. The guide needles can have an outer diameter (e.g., in the slidably mounted or piercing section) ranging, e.g., from more than about 2 cm to about 0.5 mm, from about 1 cm to about 0.6 mm, from about 5 mm to about 0.7 mm, from about 2 mm to about 0.8 mm, or about 1 mm. In many embodiments, the guide needle can essentially have the structure of a cannula or a hypodermic needle, e.g., ranging in size from 5 gauge to 30 gauge, from 8 gauge to 24 gauge, from 10 gauge to 20 gauge, from 12 gauge to 18 gauge, or 16 gauge.

Guide needles can have a piercing end configured to pierce structures, such as skin, wall structures, membranes, vessel walls, and the like. The typical piercing end is a pointed beveled end, such as those used for hypodermic needles. In some embodiments, the beveled tip can include two or more sections with different bevel angles. In alternate embodiments, the guide needle can be hollow with a central slidably mounted wire having a conical piercing tip or solid with a conical piercing tip. In many embodiments, it is preferred the guide needle have a central axial lumen so that entry into a vessel can be detected as vessel fluid appearing at the proximal end of the needle.

Guide needles commonly have a hub structure at the proximal end. Hubs typically have a greater inner diameter and/or outer diameter than the more proximal sections of the needle. In one embodiment, the needle hub is a clear chamber or "flash cup" flaring out from the proximal end of the needle, e.g., so that fluids can be viewed passing to or from the needle bore. In some embodiments, the chamber can include a gas vented membrane to prevent escape of liquid fluid from the proximal end of the needle. The needle hub can include fittings, such as a luer lock structure for connection to external devices, such as syringes.

The guide needle hub can optionally provide structures that interact with proximal hubs of the device dilator and/or catheter. For example, the needle hub can include tangs, grooves or cavities that interact with other hub structures to control or limit movement of the needle relative to other device structures. In some embodiments, the needle hub can have a structure configured to receive a mechanical force or pressure, e.g., intended to cause the needle to retract within a dilator, as will be described in detail below.

Guide Dilators

Guide dilators are typically employed in the devices for catheter insertion to provide a dilating structure slidably mounted over a guide needle and having an outer diameter expanding away (tapered) from the distal tip. Such a structure can smoothly and painlessly enlarge a hole in a vessel wall initially made by the guide needle. In many embodiments, the guide dilator provides a support structure or path to lead a catheter into the vessel. Guide dilators can include a hub configured, e.g., for interaction with external devices and/or for positioning control relative to other device components.

Guide dilators are typically flexible or resilient hollow structures with a tapered distal end. In most embodiments of the invention, the guide dilator is slidably mounted over a guide needle and also slidably mounted within a catheter. The guide dilators can be made from a flexible material, such as, e.g., silicone rubber, polypropylene, rubber, fluorocarbon plastics, and the like. In other embodiments, the dilator can be made from rigid materials. The guide dilator can be opaque or optionally translucent or transparent, e.g., to allow viewing of blood in the device lumen. Guide dilators can fit closely over guide needles of the device, e.g., touching the needle, functionally sealed over the needle, and/or within a small distance (e.g., spaced less than 20 um) from the needle. Guide dilators can range in length, e.g., from about 15 cm to about 0.7 cm, 10 cm to about 1 cm, from about 7 cm to about 2 cm, from about 5 cm to about 3 cm or about 4 cm. The guide dilators can have an inner diameter (e.g., in the section slidably mounted over the needle) ranging, e.g., from about 2 cm to about 0.5 mm, from about 1 cm to about 0.6 mm, from about 5 mm to about 0.7 mm, from about 2 mm to about 0.8 mm, or about 1 mm. In many embodiments, the dilator has a wall thickness configured to expand a vessel entry hole. The distally thin dilator wall can thicken proximally to a thickness ranging, e.g., from about 0.1 mm to about 1 cm, from about 0.5 mm to about 5 mm, from about 0.75 mm to about 2 mm, or about 1 mm.

A lubricant material can be applied to the inner surface of the dilator lumen and/or the needle outer surface to enhance sealing and/or reduce friction between the device components. The lubricant can include, e.g., silicone oil, silicone grease, mineral oil, vegetable oil, and/or the like.

Guide dilators can have a tapered distal end configured to dilate structures, such as skin, wall structures, membranes, vessel walls, and the like. In preferred embodiments, the tapered distal tip is relatively thin walled and closely contacts or seals over the outer surface of the needle distally. The wall thickness (and outer dilator wall diameter) progressively increases proximally from the tip. In many embodiments, the dilator outer diameter reaches a desired size (e.g., about the inner diameter of an associated catheter) and continues proximally for some distance with the same outer diameter. The distance from the tapered distal tip of the dilator to the final maximum distal outer diameter (dilator tapered section) typically ranges from about 30 cm to about 1 mm, from about 20 cm to about 2 mm, from about 10 cm to about 2 mm, from 7 mm to about 3 mm or about 4 mm.

Guide dilators often have a hub structure at the proximal end. The hub typically has a greater inner diameter and/or outer diameter than the more proximal sections of the dilator. In some embodiments, the chamber can include a valve or resilient membrane to seal the needle in use and/or to seal the inner bore of the dilator from the external environment should the needle be withdrawn from the device. The dilator hub can include fittings, such as a luer lock structure for connection to external devices, such as syringes.

The guide dilator hub can optionally provide structures that interact with proximal hubs of the device needle and/or catheter. For example, the needle hub can include tangs, grooves or cavities that interact with other hub structures to control or limit movement of the needle or dilator relative to other device structures. In some embodiments, the dilator hub can have a space holding, e.g., a spring element under tension or expandable material, e.g., to provide a working mount and working force to actuate a needle retraction into the dilator, as will be described in more detail below.

IV-Catheters

Catheters of the inventive devices are, e.g., working devices and/or access ports intended for insertion into a vessel. The catheters are typically slidably mounted over the guide dilator of the device and have an outer diameter expanding away (tapering) from the distal catheter tip. The catheter typically also has constant diameter conduit body proximal to the tapered tip. Such a structure can smoothly and painlessly further enlarge a hole in a vessel wall initially made by the guide needle and expanded by the dilator. In many embodiments, a rigid or flexible catheter can be guided through a vessel wall and/or some distance along the vessel lumen following the path of the guide dilator. Catheters can include a hub configured, e.g., for interaction with external devices and/or for positioning control relative to other device components.

Catheter components of the devices are typically flexible or resilient hollow structures with a tapered distal end. In most embodiments of the invention, the catheter is slidably mounted over a guide dilator. The catheters can be made from a flexible material, such as, e.g., silicone rubber, polypropylene, rubber, fluorocarbon plastics, and the like. In other embodiments, the catheter can be made from rigid materials, such as stainless steel, a glass, ceramic, rigid plastic, etc. The catheter can be opaque or optionally translucent or transparent, e.g., to allow viewing of blood in the device lumen. Catheters can fit closely over guide dilators of the device, e.g., touching the dilator, functionally sealed over the dilator, or within a small distance (e.g., spaced less than 20 um) from the dilator outer surface. A lubricant can be present between the catheter and dilator. Catheters can range in length, e.g., from about 15 cm to about 0.7 cm, 10 cm to about 1 cm, from about 7 cm to about 2 cm, from about 5 cm to about 3 cm or about 4 cm. The catheters can have an inner diameter (e.g., in the section slidably mounted over the dilator) ranging, e.g., from about 3 cm to 0.4 mm, from about 2 cm to about 0.5 mm, from about 1 cm to about 0.6 mm, from about 5 mm to about 0.7 mm, from about 2 mm to about 0.8 mm, or about 1 mm. Outer diameters and lengths of the catheter are typically greater for trocar embodiments than for IV embodiments. Catheter wall thickness is typically configured to suit the intended function of the catheter. The catheter wall typically ranges from about 0.1 mm to about 1 cm, from about 0.5 mm to about 5 mm, from about 0.75 mm to about 2 mm, or about 1 mm.

Catheters of the invention usually have a tapered distal end configured similarly to the dilator component for further dilation of structures, such as skin, wall structures, membranes, vessel walls, and the like. In preferred embodiments, the tapered distal catheter tip is relatively thin walled and closely contacts or seals over the outer surface of the dilator distally. The wall thickness (and outer catheter diameter) can progressively increase proximally from the tip for some distance. In many embodiments, the catheter outer diameter reaches a desired size (e.g., for performance of the desired catheter function) and continues proximally for some distance with the same outer diameter. The distance from the tapered distal catheter tip to the final maximum distal outer diameter (catheter tapered section) typically ranges from about 30 cm to about 1 mm, from about 20 cm to about 2 mm, from about 10 cm to about 2 mm, from 7 mm to about 3 mm or about 4 mm.

Catheters usually have a hub structure at the proximal end. The catheter hub typically has a greater inner diameter and/or outer diameter than the more proximal sections of the catheter. In some embodiments, a chamber of the catheter hub can include a valve or resilient membrane to seal the dilator in use and/or to seal the inner bore of the catheter from the external environment should the dilator be withdrawn from the device. The catheter hub can include fittings (such as, e.g., a luer lock structure) for connection to external devices, such as syringes, IV fluid conduits, surgical devices, electrodes, diagnostic devices, and/or the like.

The catheter hub can optionally provide structures that interact with proximal hubs of the device needle and/or dilator. For example, the catheter hub can include tangs, grooves or cavities that interact with other hub structures to control or limit movement of the needle or dilator.

Automatic Needle Retractors

The devices for inserting catheters can include components for retraction of the guide needle into the dilator, e.g., after the dilator has entered the vessel. In some embodiments, the retractor can automatically retract the needle on contact with a fluid from the vessel.

Needle retractors generally include a source of mechanical force in a structure configured to retract a slidably mounted needle proximally into a dilator. In some embodiments, the retraction can be directly initiated by a technician at the proper time. In preferred embodiments, the retraction is initiated by contact of a vessel fluid with a release mechanism, such as, e.g., a fluid sensitive detent or a fluid expandable material.

In a spring-loaded embodiment, a compressed spring is held under tension between a surface of a needle hub and a dilator hub. A catch can be designed such that it prevents the spring from moving the needle proximally relative to the dilator. In a manually actuated embodiment, the catch can be withdrawn by a technician allowing the spring force to drive the needle proximally. For example, the technician can directly withdraw the catch from interfering in the movement of the needle, or the technician can push or pull a lever or button mechanically associated with the catch to withdraw the catch. The retraction mechanism can further include components to direct and/or stop the retraction, as shown, e.g., in FIG. 5.

Figure 14:
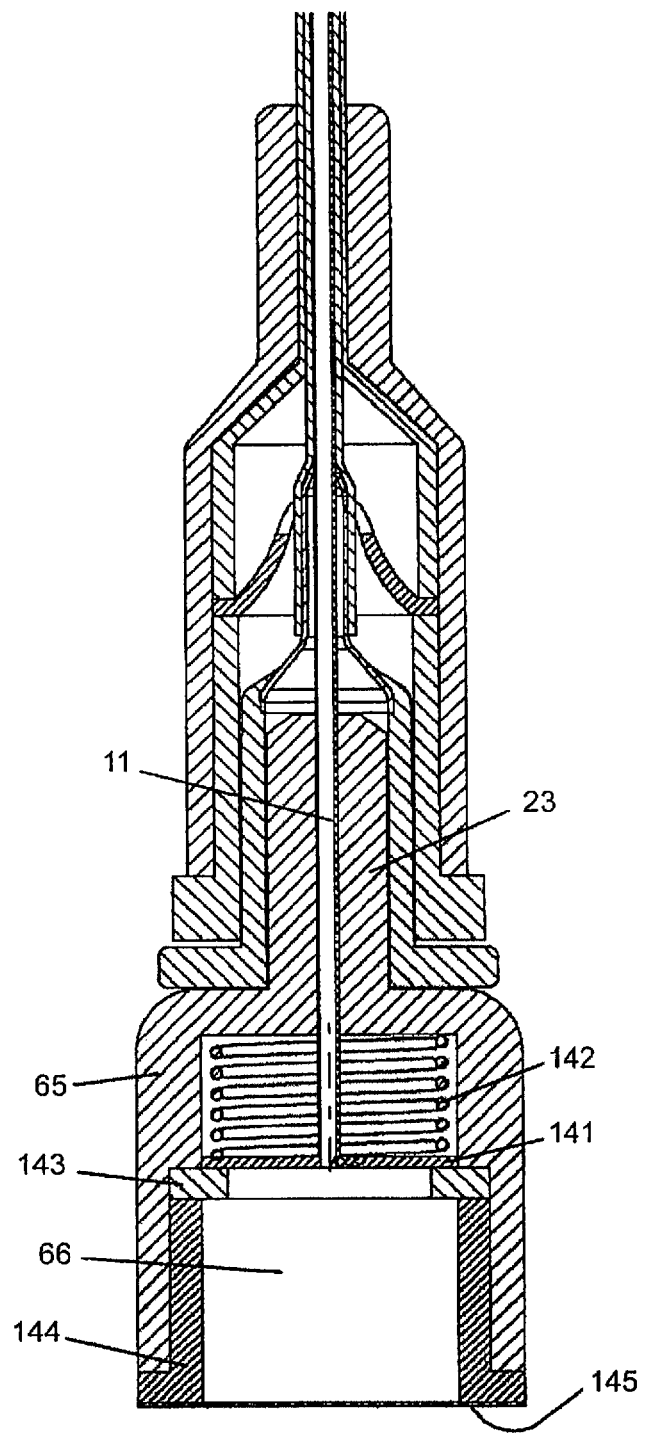
FIG. 14 shows a schematic sectional view of an exemplary needle retraction mechanism using a spring force and controlled by a releasable catch.

In a preferred embodiment, as shown in FIG. 14, the retraction of the needle can be controlled by a catch that is sensitive to contact with a fluid from the vessel. In one embodiment, the catch is held in place by a "glue" that softens or dissolves on contact with a solvent in the vessel fluid. In another embodiment, the catch is fabricated from a material that is rigid but softens in the presence of the vessel fluid. For example, the needle hub can be a piston backed by a spring urging it to slide in a dilator hub cylinder, but stopped by a ring of catch material mounted in the dilator hub wall. When fluid from the needle flows into the dilator cylinder to contact the catch material, it softens or melts, thus losing structural strength allowing the spring to push the needle proximally. In a preferred embodiment, the proximal end of the needle can incorporate a piston backed by a spring inside the flash cup urging the needle to slide in the guide needle hub and dilator hub cylinder, but stopped by a ring of catch material mounted in the flash cup wall. For example, the proximal end of the needle can incorporate a piston backed by a spring inside the flash cup urging the needle to slide in the guide needle hub and dilator hub cylinder, but stopped by a ring of catch material mounted in the flash cup wall. When the fluid from the needle flows into the flash cup to contact the catch material, it softens or melts, thus releasing the needle proximal end (hub) and allowing the spring to retract the needle into the dilator bore.

Typical materials for fluid contact release catches include, e.g., dried biologic or synthetic polymers. For example, where the vessel fluid is an aqueous solution, the catch can be fabricated from dry gelatin, cellulose, sugars, or hydrophilic synthetic polymers. In preferred embodiments, the fluid sensitive catch material is porous, giving it a large surface area. The timing of catch release on fluid contact can be determined empirically and adjusted by modulation of factors, such as, e.g., spring pressure, catch material density, catch porosity, affinity of the catch material for the fluid, thickness of the catch material, and the like. In preferred embodiments, the catch is structured to retract the needle within 0.5 seconds, 1 second, 5 seconds, 10 seconds, or more after contact with the vessel fluid.

Figure 16:
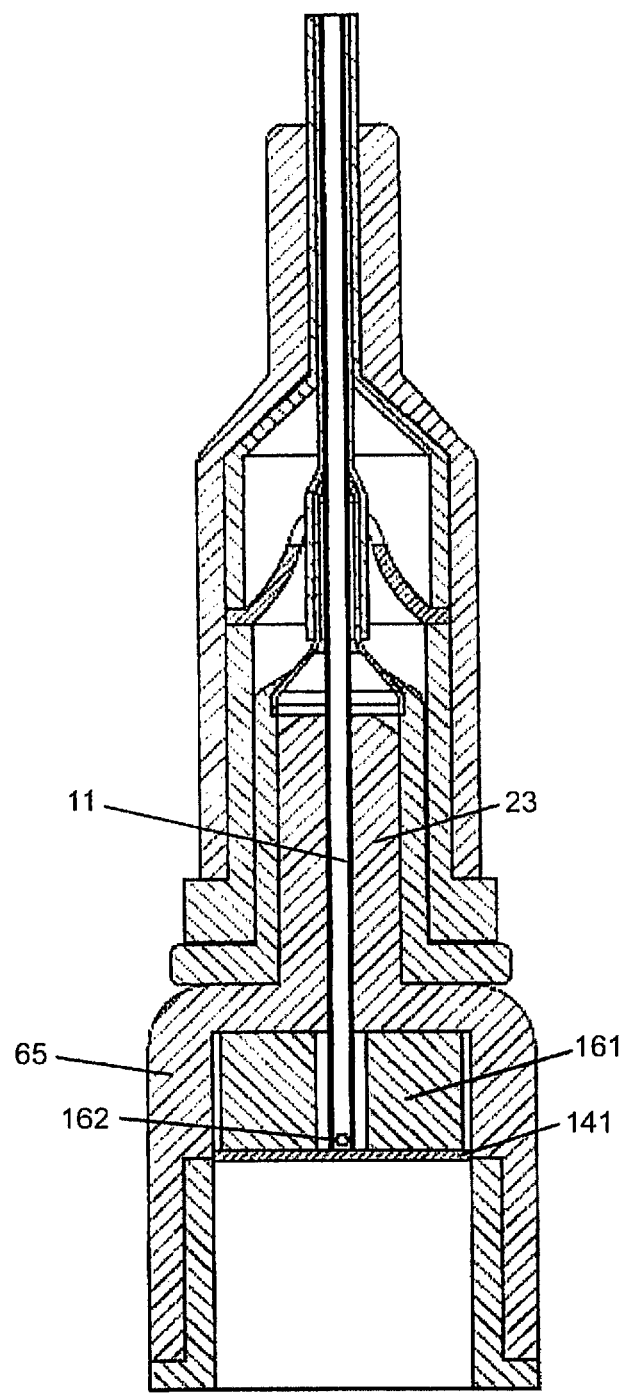
FIG. 16 shows a schematic sectional view of an exemplary needle retraction mechanism using an expandable material to move the needle relative to the dilator on contact with a vessel fluid.

In an alternate embodiment of automatic needle retraction, the force to move the needle relative to the dilator is provided by expansion of a material on contact with the vessel fluid. For example the expansion material can be positioned between the needle hub and the base of the flash cup, as shown in FIG. 16, so that of the material causes the needle to move relative to the dilator. The expandable material can expand, e.g., through a chemical reaction or through absorption of the fluid. For example, the expandable material can include reactive chemicals that provide a gaseous product on contact with the fluid. In a preferred embodiment, the vessel fluid is aqueous and the expandable material is an expandable hydrophilic polymer and/or hydrophilic foam. Preferred expansion materials include, e.g., polyacrylic acid, methacrylamide dehydrated starch or cellulose, gelatin, and various chemical modifications of these and other polymers.

Methods of Inserting Catheters

The present methods of inserting catheters generally include steps a technician can take to insert a catheter using the devices for inserting catheters described above. For example, the methods can include inserting the distal piercing end of a guide needle through a patient's skin and through the wall of a blood vessel. The catheter-inserting device can be urged distally by the technician so that the distal tapered end of the dilator wedges into the vessel wall hole made by the needle and progresses to expand the hole to a larger diameter. The guide needle can optionally be retracted or withdrawn, e.g., at any time after the wedging of the dilator. The tapered tip of the catheter can be urged distally onto the vessel wall hole and progress to expand the hole to receive the cross section of the main catheter body. The dilator can progress to guide the catheter deep into the vessel, or optionally be withdrawn after the tip of the catheter has entered the vessel. The methods can optionally involve methods of needle retraction control and/or methods of vessel fluid control.

In an exemplary embodiment, the methods include provision of a catheter insertion device, inserting a piercing end of a guide needle into the wall of a vessel, inserting the distal end of a dilator through the wall to expand the needle insertion point, retracting the needle to some point within the dilator so it can not further injure the vessel, inserting the distal end of the catheter through the insertion point, and withdrawing the dilator and needle from within the catheter. With the catheter in place in the vessel, it can act as an access port to the vessel and any number of external devices can be connected to it.

Providing the Catheter Insertion Device

The methods of inserting a catheter can be practiced using the devices for insertion of catheters, e.g., as described herein. Briefly, insertion devices can be provided with a guide needle slidably mounted within a cylindrical guide dilator, which is slidably mounted within a cylindrical catheter. The three components can each comprise a tapered distal tip and/or a proximal hub. The tapered tips can be configured to pierce and/or dilate a hole in the wall of a vessel. The hubs can be configured to accommodate technician handling of the device, control relative movement of the three components and/or functionally interact with external devices.

In a preferred embodiment, provision of a catheter insertion device includes assembly of a device by sliding a needle into a dilator so that the piercing end of the needle extends out from the distal end of the dilator, and so that retraction actuating and/or retraction limiting features of the needle hub functionally interact with complimentary features of the dilator hub, as described above. The dilator can be slid into the catheter through a slitted resilient membrane so that the dilator outer surface is hermetically sealed in the catheter hub and the tapered tip of the dilator extends out from the distal end of the catheter. In use, the distal ends of the three components are inserted into a blood vessel, the needle is retracted automatically and/or to a controlled extent, the dilator is withdrawn while the inner aspects of the catheter are sealed by the membrane from the external environment, and external devices are attached to the catheter.

Inserting the Device

Methods of placing a catheter include steps of inserting the three components (needle/dilator/catheter) into a vessel. The guide needle functions to make the initial pierced hole in the skin or vessel wall. The dilator can follow the needle to expand the size of the hole to allow entry of the catheter and/or can be structured to function as a guide to direct the catheter some desired distance within the vessel. The catheter is typically inserted last and can further expand the hole and/or can be designed to remain in place within the vessel after the needle and/or dilator are removed from the vessel.

The piercing end of the needle can be inserted into the wall of a vessel, e.g., in a manner similar to insertion of a hypodermic needle or old art catheter. Typically the piercing end of the guide needle is inserted through a patient's skin at a point overlying a blood vessel to be catheterized. The dilator and catheter can follow before piercing the vessel, but the needle typically pierces the vessel before the catheter enters the skin. The guide needle acts as an insertion guide for the dilator and in many cases the needle has pierced both the skin and vessel before the dilator has entered the skin. Because the guide needle is rigid, it provides the technician with a topological certainty and structural strength required to confidently manipulate the device and complete the required mechanical tasks.

The guide dilator is supported and directed by the guide needle for insertion into the vessel and for dilation of the entry hole. Once the dilator has entered the vessel, the needle can be retracted so that the piercing end is covered by, e.g., softer and more resilient material of the dilator to avoid piercing of an opposite vessel wall by the needle. In some embodiments, the needle is initially only retracted to within the dilator, but not retracted to a point outside the vessel. With this arrangement, the needle can continue to provide a rigid tool for the technician to manipulate progression of the dilator and provide solid backing to the dilator as it dilates the vessel hole to a larger diameter. In some embodiments, the needle can be held at a point within the vessel as the guide dilator slides distally to progress further into the vessel. In this way, a solid structural presence is maintained at the entry hole while the flexible dilator body progresses along the vessel, e.g., to provide a path of later insertion of the catheter. Alternately, the needle can be withdrawn entirely out of the vessel and/or entirely from the device before the dilator has completed progression and/or before the catheter has entered the vessel.

The catheter can be inserted into the vessel while the guide needle and/or guide dilator remain inserted through the vessel at the initial insertion point. The catheter can be inserted into the vessel while the distal tip of the guide needle and/or distal tip of the guide dilator are just inside the vessel and/or after a distal tip has been inserted some distance along the interior of the vessel. In a preferred embodiment, the needle is inserted some distance within the vessel and the guide dilator is just inside the vessel when the catheter is inserted through the vessel wall. In a preferred embodiment, the catheter is inserted through the vessel wall with both the guide dilator and the guide needle inserted some distance (e.g., 1 cm, 2, cm, 5 cm 10 cm or more) along the vessel. In a more preferred embodiment, the catheter is inserted through the vessel wall while both the guide needle and guide dilator are just inside (e.g., not having progressed more than 2, 5 or 10 dilator outer diameters) the vessel. In a most preferred embodiment, the catheter is inserted through the vessel wall while the guide dilator has been inserted some distance along the vessel and the guide needle is just inside the vessel. In this way, the catheter has solid support to enter the vessel but resilient support to progress along a curving path of a fragile vessel.

Embodiments where the needle is not inserted as far as the dilator can be accomplished by slidable retraction of the needle to a point within the dilator, or by complete withdrawal of the needle while the dilator remains in the vessel, With the needle retracted, the flexible dilator tip can facilitate progression along the vessel while minimizing the likelihood of trauma to the vessel interior.

EXAMPLES

The following examples are offered to illustrate, but not to limit the claimed invention.

Example 1

A Catheter Insertion Assembly

An exemplary catheter insertion assembly can be manufactured including a guide needle for perforation of skin and vessel; a guide dilator to expand the needle perforation, protect the vessel from further perforations and to guide a catheter into the vessel; and, a catheter to provide access to the vessel by clinical technicians.

FIG. 1 shows a catheter insertion assembly 10 composed of a guide needle 11, typically formed from stainless steel; a guide dilator 12, typically a tough, flexible plastic such as polyurethane or polytetrafluoroethylene; and, an intra-vascular catheter 13, also produced from a tough, flexible material, and of a geometry needed for a given medical procedure. These three components of the invention are fitted together concentrically such that the distal end 14 of the guide needle protrudes from the distal end 15 of the guide dilator, and the guide dilator protrudes from the distal end 16 of the intra-vascular catheter.

Figure 2:
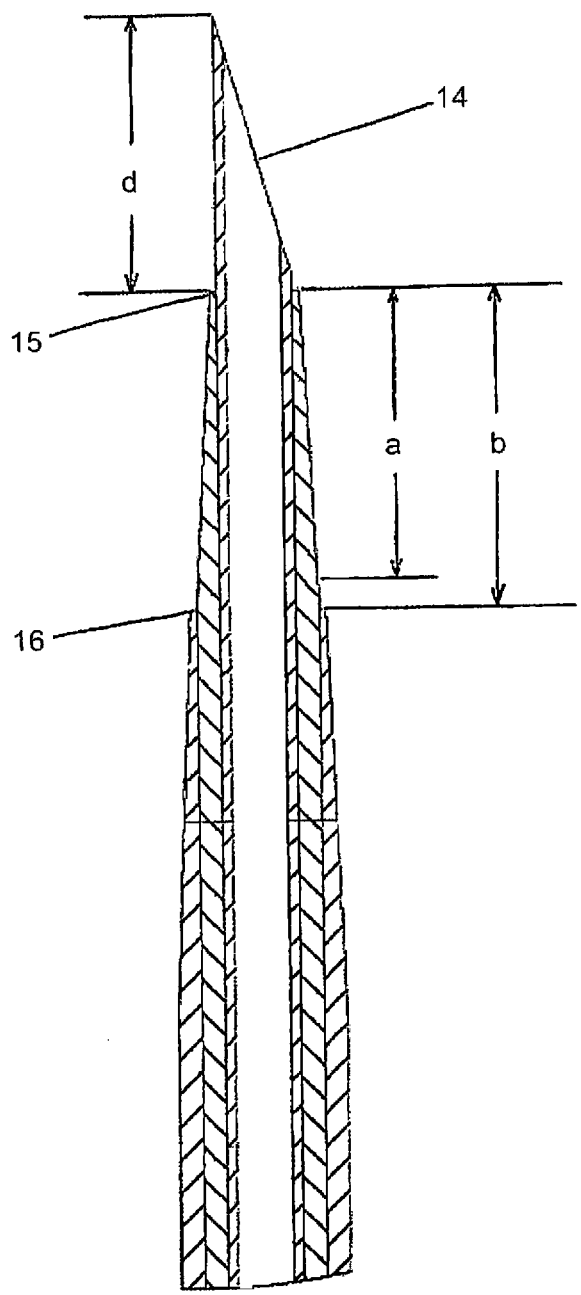
FIG. 2 is a cross sectional view of an exemplary device distal end showing, in detail, the distal end of the guide needle, the guide dilator, and the intra-vascular catheter.

A detail view of this embodiment is shown in FIG. 2, wherein the distal end 14 of the guide needle contains a beveled tip for the puncturing of the patient's skin and targeted vessel. Any tip geometry suitable for such purpose can be utilized. The distal end 15 of the guide dilator is tapered to enlarge the pierced portal created by the guide needle as the vessel is punctured. The length, "a", of the tapered section may vary, depending on the bore diameter of the intra-vascular catheter being placed, but should be less than or equal to the distance, "b", that the distal end of the guide dilator protrudes from the distal end 16 of the intra-vascular catheter. The distal end of the intra-vascular catheter is also tapered so as to minimize the force required for the catheter to penetrate the patient's skin and enlarge the portal in the targeted vessel wall. Although shown with tapering of one component immediately following tapering of the next component, the device can optionally include segments of constant outer diameter some distance before the tapered tip of the next component.

Figure 3:
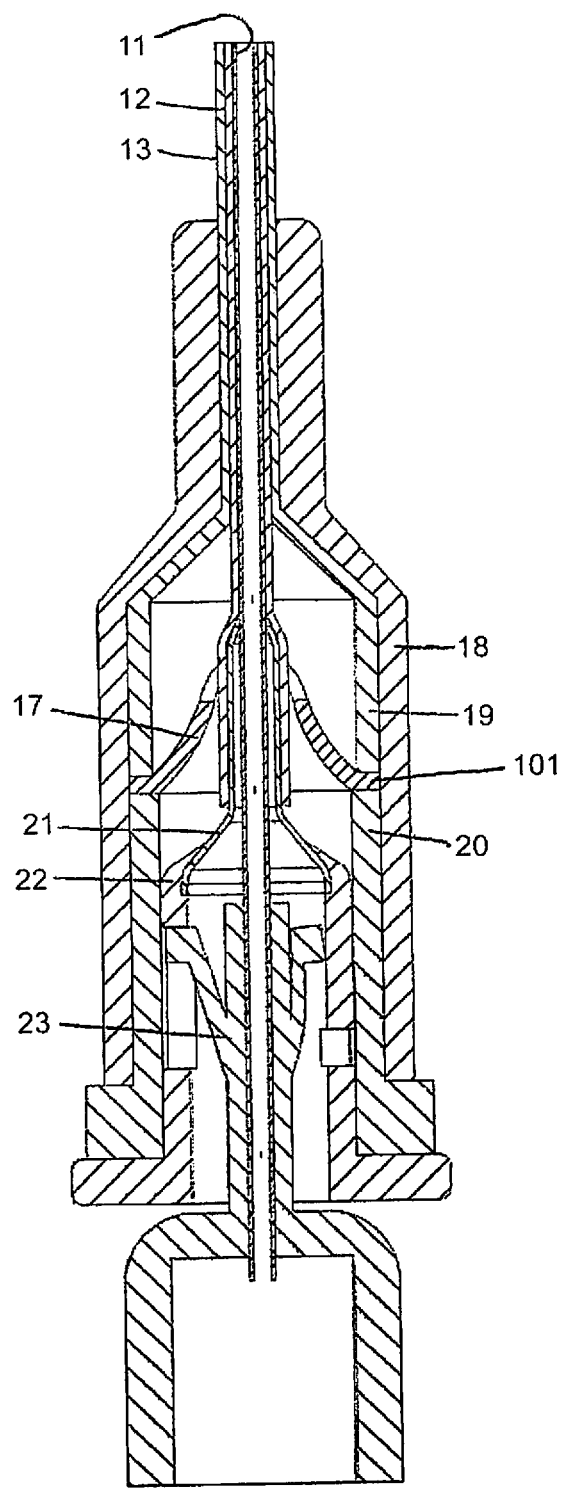
FIG. 3 is a cross sectional view of an exemplary device proximal end showing, in detail, the catheter body, the guide needle, the guide dilator, the intra-vascular catheter, the one way valve, and the catheter body plug.

FIG. 3 provides a detailed view of an embodiment showing the design and relative positions of the guide needle 11, the guide dilator 12, the intra-vascular catheter 13, and the one way valve 17. The one way valve is produced from a tough, flexible, elastic (resilient) material such as natural rubber, silicone rubber, or thermoplastic elastomer so that the opening in the one way valve can open, stretch, and form a fluid-tight seal around the guide dilator, but then contract and close when the guide dilator is withdrawn. The outer flange of the one way valve is held in its position inside the catheter body 18 between the proximal end of the intra-vascular dilator 19 and the catheter body plug 20. The proximal end of the intra-vascular catheter and the catheter hub plug are positioned concentrically within the catheter body so that their outside surfaces form a fluid-tight and mechanically strong attachment to the inside surface of the catheter body using either a tight dimensional fit or suitable adhesive. The guide dilator hub base 21 is formed from stainless steel tubing in this embodiment of the invention, and is molded into the guide dilator hub body 22. The guide dilator hub body is made of a hard, rigid plastic, such as, e.g., polycarbonate, nylon, polystyrene, or polyester, with good dimensional stability. The guide needle hub 23 is attached to the guide needle forming a fluid-tight and mechanically strong attachment to each other. The guide needle hub is made from a hard, rigid, transparent plastic with good dimensional stability and dissimilar composition from the guide dilator hub to allow its outer surface to slide against the inner surface of the catheter hub. The operation of this embodiment of the invention is discussed in the remaining illustrations.

Figure 4:
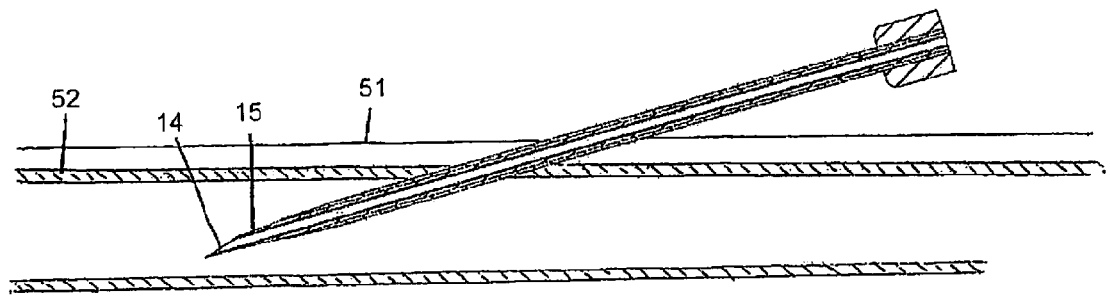
FIG. 4 is a cross sectional view of one embodiment of the present invention showing the distal end of the guide needle and the guide dilator puncturing the skin and targeted vessel.

In FIG. 4, the distal end of the guide needle 14 and guide dilator 15 are shown to penetrate the skin 51 and targeted vessel 52. The portal created by the guide needle is elastically enlarged by the distal end of the guide dilator 15 to create a fluid tight fit between the vessel wall and guide dilator.

Example 2

Needle Retraction Limiter

Figure 5:
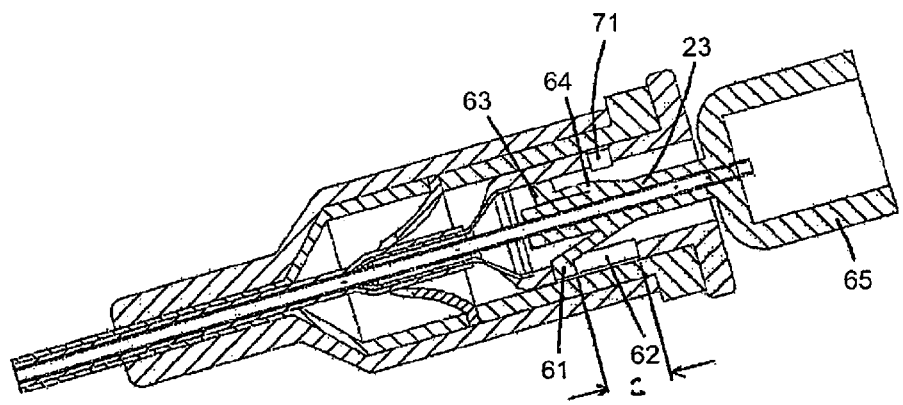
FIG. 5 is a sectional view of one embodiment of the present invention showing the positions of guide needle hub, the one way valve, and the guide dilator and intra-vascular catheter hubs when the tip of the guide needle and guide dilator are puncturing the skin and targeted vessel.

In FIG. 5, the guide needle hub, the guide dilator hub, the one way valve, and the catheter hub are shown in their typical relative positions at the time the distal end of the guide needle and catheter are manipulated to penetrate the skin and vessel wall as described in FIG. 4. The guide needle hub 23 contains two molded tangs, one 61 of which fits into a slot 62 in wall of the guide dilator hub. The slot limits the travel of the tang, and therefore limits the travel of the guide needle relative to the guide dilator. The open length of the slot, "c", is greater than the distance that the distal end of the guide needle protrudes from the distal end of the catheter guide; length "d" in FIG. 2. The second tang 63, attached to the guide needle hub, is squeezed against the inner wall of the guide dilator hub, such that the arm 64 of the tang is under tension in a bent mode. The elastic nature of the plastic used to produce the guide needle hub causes the tang to apply a small force against the inner wall of the guide dilator hub, although that force does not inhibit axial movement of the guide needle hub within the guide dilator hub. Having penetrated the targeted vessel, the guide needle fills with blood forced by the patient's blood pressure. The blood flows into the transparent guide needle hub and into the flash cup 65. A breathable paper filter or similar membrane may be installed in the flash cup to allow the blood to flow into the flash cup without leaking out. Seeing the blood flow, the caregiver can determine that the targeted vessel has in fact been punctured with the guide needle. Further safe placement of the catheter device may then proceed, starting with the retraction of the guide needle tip into the distal end of the guide dilator.

Figure 6:
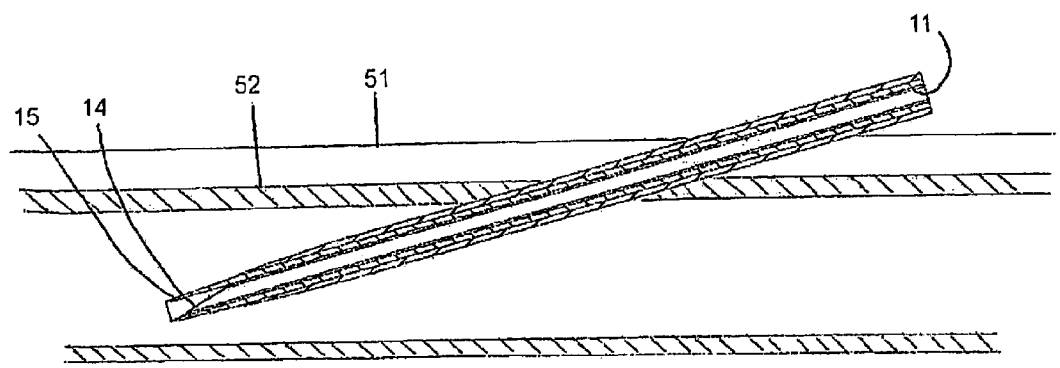
FIG. 6 is a cross sectional view of one embodiment of the present invention showing the guide needle tip retracted into the distal end of the guide dilator while the catheter assembly is positioned within a vessel.

In FIG. 6, the distal end 14 of the guide needle is shown retracted into the distal end 15 of the guide dilator such that the tip of the guide needle is completely inside the distal end of the guide dilator, thereby reducing the chance of damage to the vessel as the catheter is fully inserted into the vessel.

Figure 7:
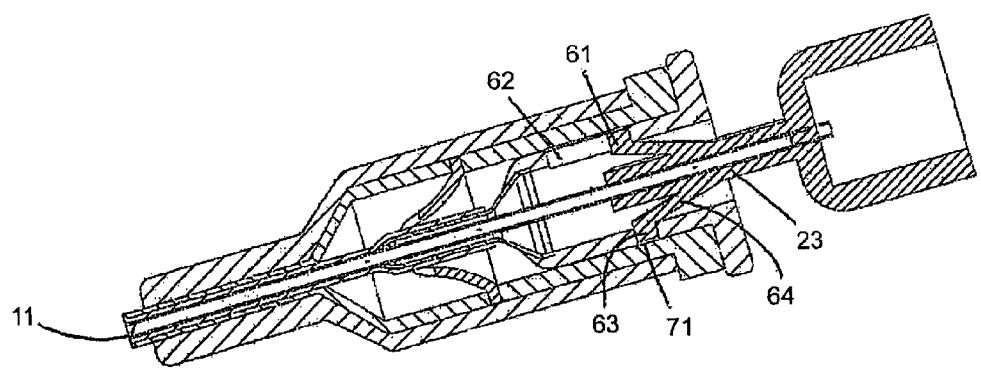
FIG. 7 is a cross sectional view of one embodiment of the present invention showing positions of a guide needle hub, a one way valve, a guide dilator hub and intra-vascular catheter hub, when the guide needle tip is retracted into the distal end of the guide dilator, e.g., while the catheter assembly is positioned within a vessel.

The retraction of the guide needle 11 and guide needle hub 23 are illustrated in FIG. 7. The guide needle is pulled axially from the distal end of the catheter body 18 so that the tang 61 slides in the slot 62 until it reaches the end of the slot, at which point the other tang 63 becomes positioned over an opening 71 in the guide dilator hub, having a similar shaped cross section as the tang, at which point the elastic energy in the tang arm 64 is released and the tang 63 is pushed into the opening 71, locking the guide needle into the guide dilator hub and prevent any movement of one relative to the other. After the guide needle is locked into the guide dilator hub as shown in FIG. 7, final positioning of the intra-vascular catheter can be safely achieved without danger of re-puncturing or damaging the vessel wall.

Example 3

Withdrawal of Guides from the Assembly

Figure 8:
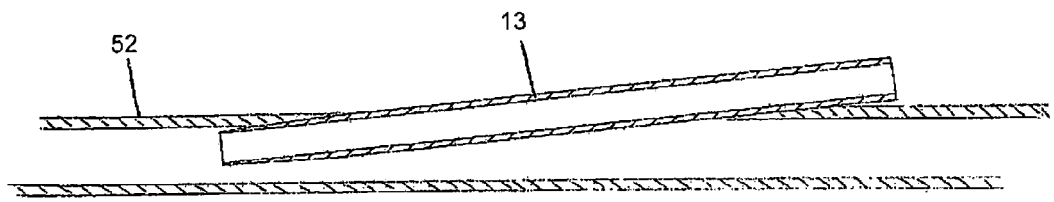
FIG. 8 is a cross sectional view of one embodiment of the present invention showing the distal end of the intra-vascular catheter with the guide dilator fully withdrawn leaving the intra-vascular catheter in position within the vessel.

Once the intra-vascular catheter is in position, the catheter body is held and further outward axial pressure on the guide needle allows the guide needle and guide dilator to be withdrawn from the catheter body/intra-vascular catheter/catheter body plug assembly. FIG. 8 shows the intra-vascular catheter 13 has been positioned fully in the targeted vessel 52 and the guide dilator and guide needle completely withdrawn.

Figure 9:
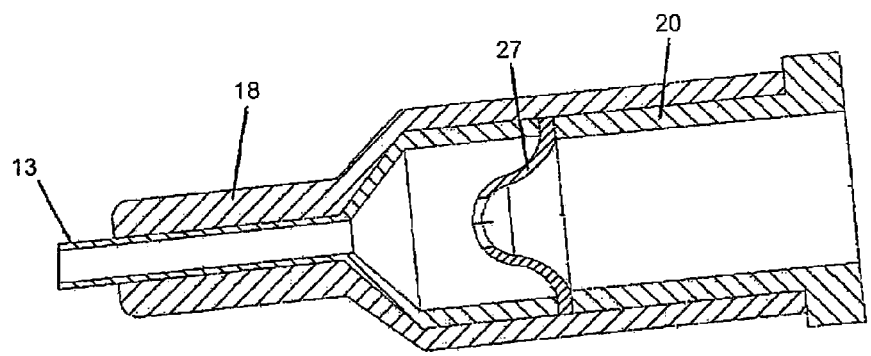
FIG. 9 is a cross sectional view of one embodiment of the present invention showing the intra-vascular catheter hub and one way valve after the guide dilator has been fully withdrawn from the IV catheter.

FIG. 9 shows the corresponding view of the catheter body, the intra-vascular catheter, the catheter body plug, and the one way valve with its opening completely closed.

Figure 10:
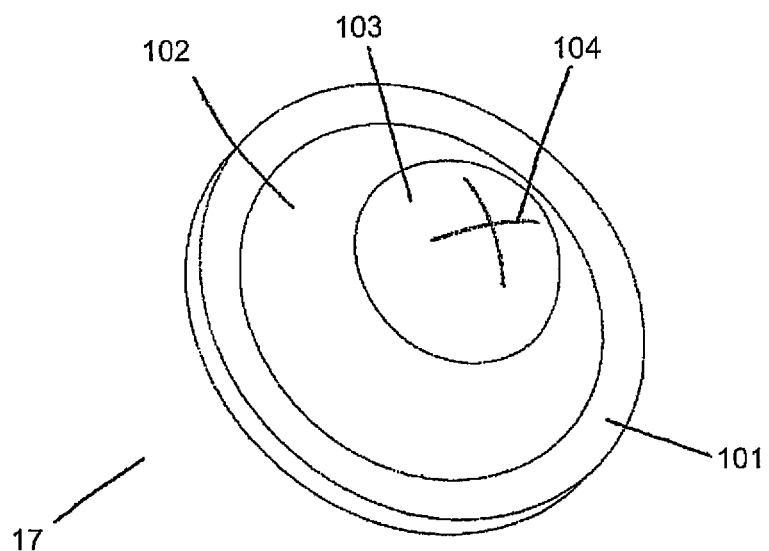
FIG. 10 is a detail view of a catheter valve, e.g., as it may appear after the guide dilator is withdrawn.

FIG. 10 shows an oblique view of the one way valve 17. The valve is composed of an outer flange 101, where it is held in position by the proximal end of the intra-vascular catheter and the catheter body plug; a generally conical shaped body 102 to make mechanical penetration easy in one direction and more difficult in the other; a rounded apex 103 in the cone that, when the outer surface is subjected to the hydrostatic pressure of blood, forces the orifice closed, preventing blood from passing through; and an orifice 104 composed of a slit or series of slits that converge at the apex of the cone, forming the opening through which the guide dilator or an intra-vascular fluid fitting may be placed.

Figure 11:
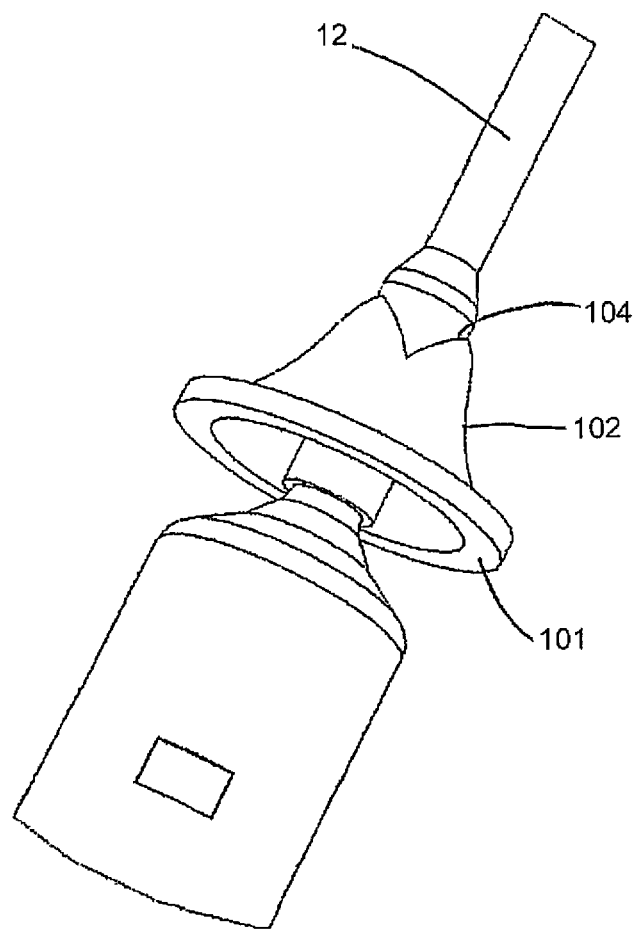
FIG. 11 is a detail view of a catheter valve as it appears sealing about a guide dilator.

FIG. 11 shows an oblique view of the one way valve 17 with the guide dilator 12 penetrating the valve orifice 104. The projected length of the slit or slits is less than the diameter of the guide dilator, so that the edges of the open slit must elastically stretch and form a tight seal around the outer surface of the guide dilator, preventing blood from leaking between the valve and the guide dilator. When an intra-vascular fluid fitting is inserted into the catheter, the cylindrical end of the fitting pushes into the conical body of the one way valve, causing the slits in the apex of the conical end of the valve to separate and allow the intra-vascular fluid to flow through the intra-vascular catheter and into the patient as prescribed in their treatment.

Example 4

Reduced Forces in Catheter Placement

A unique aspect of the invention is the placement of an intra-vascular catheter without causing as much pain to the patient as occurs when current intra-vascular catheter technology is used. While pain is a subjective sensation that varies from patient to patient, a relative indicator of pain associated with intra-vascular catheter placement is the amount of force needed to insert the guide needle and place the intra-vascular catheter, as discussed above. Therefore, to demonstrate the reduction of pain generated with the placement of invention, a sensitive force transducer was attached to the proximal end of an intra-vascular catheter body to measure the force required to penetrate the skin of a ripened seedless naval orange. (Nurses interviewed by the inventors reported that the exercise of puncturing an orange with an intra-vascular guide needle and catheter approximates the "feel" or force needed to puncture human skin and a targeted vessel with the device.) A comparison of insertion forces for a commercial 18 gauge intra-vascular catheter and a prototype model of the current invention was made.

Figure 12:
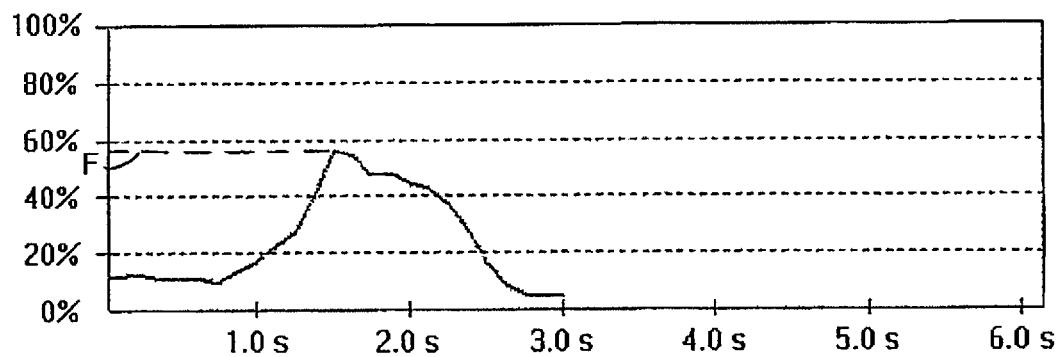
FIG. 12 is a graph showing of force required as a function of time as an old art 18 gauge guide needle and catheter to puncture the flesh of an orange.

The commercial 18 gauge intra-vascular catheter is composed of a needle with a beveled tip. The needle has a 0.035 inch outside diameter. The intra-vascular catheter has a tapered tip at its distal end, with a final outside diameter of 0.047 inch. A nurse, experienced in administering intra-vascular catheters, made insertions of the commercial intra-vascular catheter into different places in the orange. An example of the force required for the insertion of the commercial 18 gauge catheter into the orange, measured as a function of time, is shown in FIG. 12. The force scale is shown on the vertical axis in arbitrary units of percentage. Calibration weights were used to convert the force units into grams. The peak force (F) was recorded as the insertion was executed. A total of 10 insertions were made to account for slight differences in technique and variations in the texture of the orange being punctured. The average peak force required for insertion of the 18 gauge guide needle and catheter was 123 grams.

The prototype model of the current invention was constructed of a guide needle having a beveled tip and an outside diameter of 0.022 inch. The guide dilator had a tapered distal end and a final outside diameter of 0.034 inch. The intra-vascular catheter had a tapered distal end and a final outside diameter of 0.048 inch. This prototype intra-vascular catheter was inserted 10 times into different locations in the same orange by the same nurse using the process described above for the commercial 18 gauge catheter.

Figure 13:
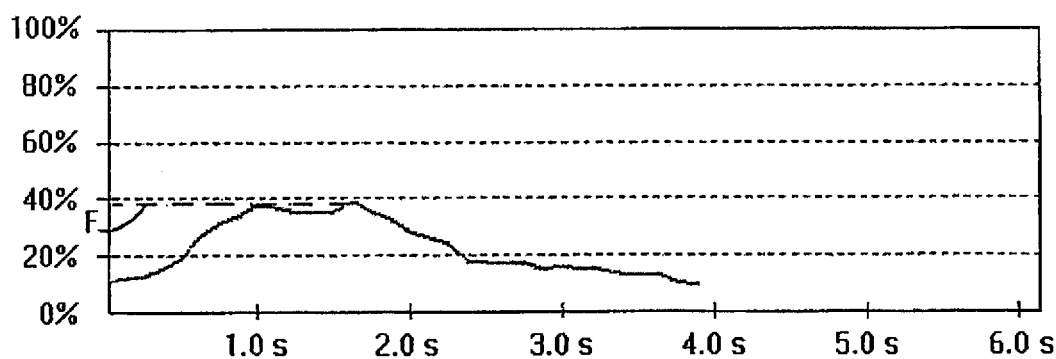
FIG. 13 is a graph showing the amount of force required as a function of time for the needle, dilator and catheter of the present invention to puncture the flesh of an orange.

An example of the force required for the insertion of the prototype guide needle and catheter into the orange, measured as a function of time, is shown in FIG. 13. The force scale is shown on the vertical axis in arbitrary units of percentage. Calibration weights were used to convert the force units into grams. The peak force (F) was recorded as the insertion was executed. The average peak force required for insertion of the prototype guide needle and catheter was 97 grams, or 21% less than the force required for insertion of the conventional 18 gauge guide needle and catheter.

In another embodiment of the current invention the guide needle and guide dilator may be designed to fit inside a larger or smaller intra-vascular catheter. For example, a 16 gauge intra-vascular catheter that has an outside diameter of 0.062 inches and an inside diameter of 0.050 may be designed with a guide dilator having a tapered distal end and a final outside diameter of 0.049 inch and a guide needle having a beveled tip and an outside diameter of 0.037 inch.

Similarly, a 22 gauge intra-vascular catheter that has an outside diameter of 0.034 inch may be designed with a guide dilator having a tapered distal end and an outside diameter of 0.022 inch and a guide needle having a beveled tip and an outside diameter of 0.010 inch.

Example 5

Automatic Needle Retractor

An exemplary automatic needle retractor is shown in FIG. 14. In this embodiment, the outside diameter of the guide needle 11 is concentrically fit into the inside diameter of the guide needle hub 23 such that the guide needle slides axially within the guide needle hub while maintaining a liquid tight seal with the guide needle hub. A thin, disc-shaped piston 141 (a needle hub embodiment) having a through hole at the center is attached to the proximal end of the guide needle. The diameter of the piston is approximately the same as the inner diameter of the flash cup 65 within which the piston slidably is positioned. A spring 142 is held in compression within the flash cup between the piston and a catch 143. The catch is held in position within the flash cup by a flash cup end plug 144. Upon introduction of the distal end of the guide needle into a vessel, fluid from the vessel flows through the guide needle into the flash cup chamber 66, wherein the fluid contacts and softens the catch material. A filter barrier 145 is attached to the end of the flash cup end plug allowing ventilation of air displaced by the fluid entering the flash cup chamber, but preventing any leakage of liquid fluid.

Figure 15:
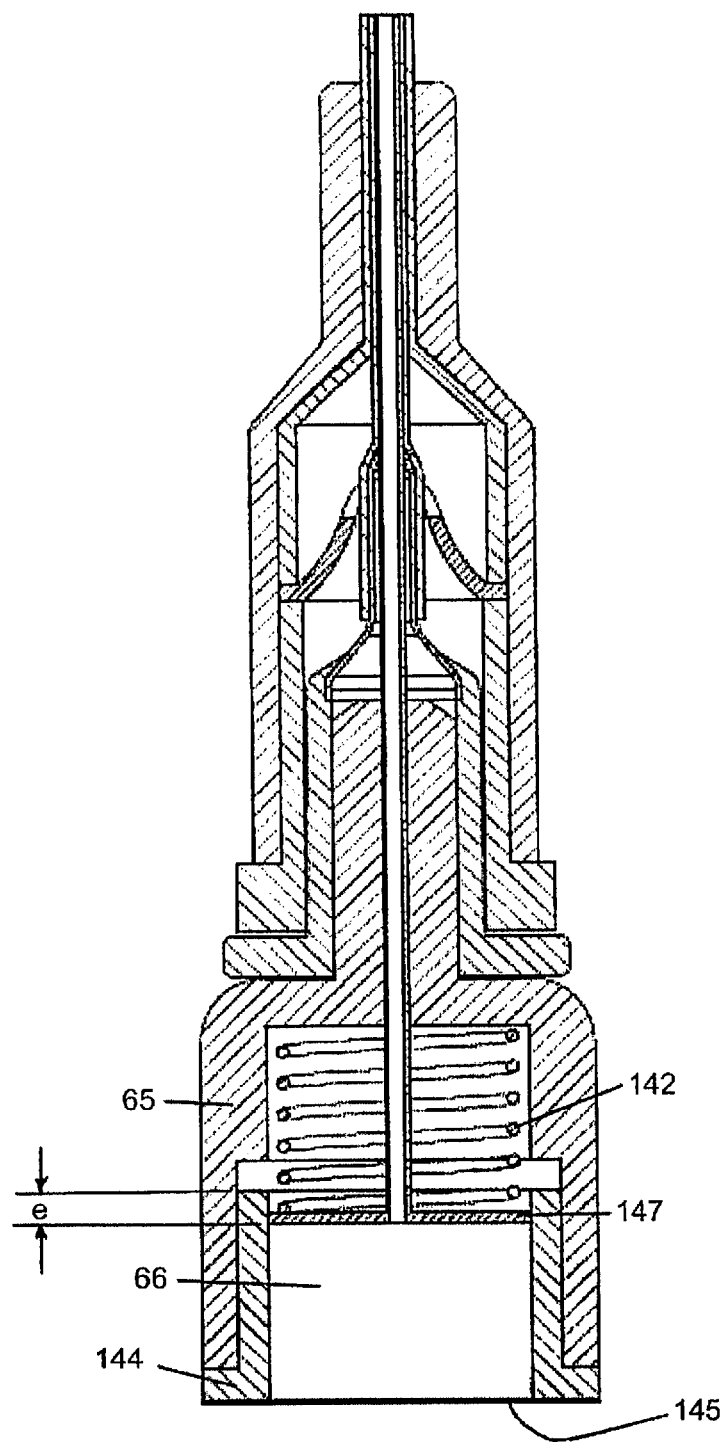
FIG. 15 shows a sectional view of a needle retraction mechanism as it may appear after the catch releases and allows the spring to retract the needle.

When the fluid contacted catch 143 softens to the point it can no longer withstand the force of the spring acting on it through the piston, the piston is forced through the catch to slide axially and proximally, as shown in FIG. 15. The piston's displacement, "e", is greater than or equal to the dimension, "d" in FIG. 2, resulting in the tip of the needle being retracted within the dilator. The retractor mechanism can further include components to direct, limit, and/or stop the retraction of the needle, as well as prevent re-emergence of the needle from the distal end of the dilator, as shown, e.g., in FIG. 5.

Example 6

Alternate Embodiment of Automatic Needle Retractor

An automatic needle retractor can also be driven by an actuator material that expands upon contact with the vessel fluid. In this embodiment, shown in FIG. 16, the outside diameter of the guide needle 11 is closely fit into the inside diameter of the guide dilator hub 23 such that the guide needle slides axially within the guide dilator hub while maintaining a liquid tight seal with the guide dilator hub. A thin, disc-shaped piston 141 is attached to the proximal end of the guide needle and forms a seal over its bore opening. The diameter of the piston is approximately the same as the inner diameter of the flash cup 65 within which the piston is positioned. An expandable actuator material 161 is held inside the flash cup by the piston. Upon introduction of the distal end of the guide needle into a vessel, fluid from the vessel flows through the guide needle and exits through one or more holes 162 in the wall of the guide needle at its proximal end, thereby directing the fluid to contact the expandable actuator material.

Figure 17:
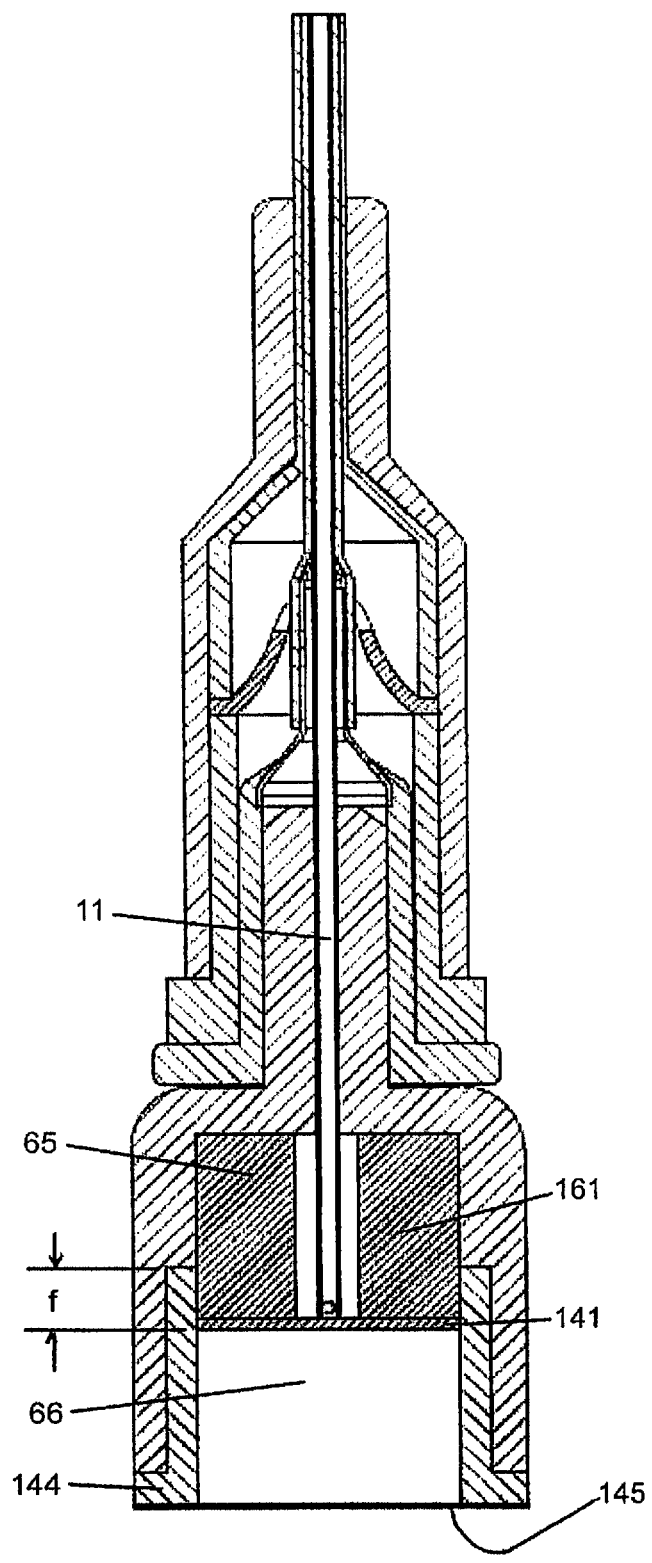
FIG. 17 shows a sectional view of the needle retraction mechanism after an expandable material has been contacted by a vessel fluid and caused the retraction of the needle.

As the actuator material expands it causes the piston, and therefore the guide needle, to be displaced axially as shown in FIG. 17. The piston's displacement, "f", is greater than or equal to the dimension, "d" in FIG. 2, resulting in the tip of the needle being retracted within the dilator. A filter barrier 145, attached to the end of the flash cup end plug 144 allows air displaced by the piston and expanding actuator in the flash cup chamber 66 to permeate while preventing any leakage of fluid. The retractor mechanism can further include components to direct, limit, and/or stop the retraction of the needle, as well as prevent re-emergence of the needle from the distal end of the dilator, as shown, e.g., in FIG. 5.

Other Examples

Another embodiment of the current invention includes a guide needle having tip geometries other than the beveled tip described in previous embodiments. Needle tip geometries may include, but are not limited to, tapered tips in which the outside diameter of the guide needle gradually increases from some small finite size at the tip to a diameter that approaches that of the inside diameter at the distal end of the guide dilator; and tapered tips in which the outside diameter of the guide needle gradually increases from some small finite size at the tip to a diameter that approaches that of the outside diameter of the guide dilator, at which point the guide needle, at which point a reduced diameter shoulder in the guide needle allows the guide dilator to fit such that the distal end of the guide dilator forms a smooth, monotonically increasing outside diameter with the outside diameter of the guide needle. The needle does not have to be hollow.

In other embodiments of the current invention, any of the components may be produced with materials other than those cited in the descriptions above, as long as the alternative materials impart a structure to provide the function required of the component individually and as a part of the complete device. For example, the guide dilator hub may be made in whole or in part of stainless steel, a rigid thermoplastic, or a combination of the two materials. Coatings or modifiers may be added to select components to give them a lubricious surface that allows them to slide against components, which are in close contact. For example, the dilator catheter may incorporate a polymer modifier that migrates to, or is deposited onto its surface, allowing the guide needle to slide freely against its inside diameter and the intra-vascular catheter to slide freely against its outside diameter.

In other embodiments of the present invention, the design of the spring tabs or tangs in the guide needle hub and the slots in the guide dilator hub that together form the catch mechanism may be varied in materials and component shapes to produce the same function. For example, the tangs, which are integrally molded of plastic as a part of the guide needle hub in the preferred embodiment, could be produced of spring stainless steel and insert molded when the guide needle hub is produced.

In still other embodiments of the present invention the catch mechanism may be designed with the spring tabs or tangs integrated into the guide dilator hub and the slots into which the tangs move to limit axial movement of the guide needle may be formed into the guide needle hub.

It is understood that the examples and embodiments described herein are for illustrative purposes only and that various modifications or changes in light thereof will be suggested to persons skilled in the art and are to be included within the spirit and purview of this application and scope of the appended claims.

While the foregoing invention has been described in some detail for purposes of clarity and understanding, it will be clear to one skilled in the art from a reading of this disclosure that various changes in form and detail can be made without departing from the true scope of the invention. For example, many of the techniques and apparatus described above can be used in various combinations.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A catheter insertion assembly comprising:
    a guide dilator comprising a hub at a dilator proximal end;
        a rigid guide needle slidably mounted within the dilator and comprising a distal piercing end, an axial bore, and a needle proximal end; and,
        an actuator capable of expanding in response to heat or moisture to urge the needle from a first position proximally relative to the dilator to a second position;
    wherein, in the first position, the distal piercing end of the needle extends out from a distal end of the dilator;
    wherein, in a second position, the distal piercing end of the needle is retracted within the bore of the dilator; and,
    whereby contact of the actuator with a warm or aqueous fluid flowing from the needle axial bore forces the needle to slide proximally relative to the dilator.

2. The assembly of claim 1, wherein the actuator is selected from the group consisting of: a hydrogel, a dry compressed foam, a shape-memory alloy, and a dehydrated hydrophilic polymer.

3. The assembly of claim 1, wherein the dilator is flexible.

4. The assembly of claim 1, further comprising a transparent chamber in fluid contact with the bore of the needle at a proximal end of the needle, whereby a fluid flowing from the bore can be observed.

5. The assembly of claim 1, further comprising a catheter slidably mounted over an outside surface of the dilator.

6. The assembly of claim 1, wherein the actuator comprises other than a spring.

7. The assembly of claim 1, wherein the actuator comprises a foam or sponge.

8. The assembly of claim 1, wherein the actuator is adapted to expand in response to contact with moisture.

9. The assembly of claim 1, wherein most of the needle within the dilator is rigid.

* * * * *